(12) United States Patent
Russell et al.

(10) Patent No.: US 9,603,787 B2
(45) Date of Patent: Mar. 28, 2017

(54) SUNSCREEN FORMULATIONS COMPRISING GEMINI SURFACTANTS AND SILICONE BASED SURFACTANTS

(71) Applicant: Akzo Nobel Chemicals International B.V., Arnhem (NL)

(72) Inventors: Michael Russell, Madison, NJ (US); Qiwei He, Belle Mead, NJ (US)

(73) Assignee: AKZO NOBEL CHEMICALS INTERNATIONAL B.V., Arnhem (NL)

(*) Notice: Subject to any disclaimer, the term of this patent is extended or adjusted under 35 U.S.C. 154(b) by 0 days.

(21) Appl. No.: 14/905,895

(22) PCT Filed: Aug. 27, 2014

(86) PCT No.: PCT/EP2014/068169
§ 371 (c)(1),
(2) Date: Jan. 18, 2016

(87) PCT Pub. No.: WO2015/028507
PCT Pub. Date: Mar. 5, 2015

(65) Prior Publication Data
US 2016/0166496 A1 Jun. 16, 2016

Related U.S. Application Data

(60) Provisional application No. 61/870,291, filed on Aug. 27, 2013.

(30) Foreign Application Priority Data
Oct. 30, 2013 (EP) ..................................... 13190946

(51) Int. Cl.
| | | |
|---|---|---|
| A61K 8/00 | (2006.01) |
| A61Q 17/04 | (2006.01) |
| A61K 8/893 | (2006.01) |
| A61K 8/39 | (2006.01) |
| A61K 8/894 | (2006.01) |
| A61K 8/34 | (2006.01) |
| A61K 8/35 | (2006.01) |
| A61K 8/37 | (2006.01) |
| A61K 8/40 | (2006.01) |
| A61K 8/81 | (2006.01) |
| A61K 8/86 | (2006.01) |

(52) U.S. Cl.
CPC ................ *A61K 8/893* (2013.01); *A61K 8/34* (2013.01); *A61K 8/35* (2013.01); *A61K 8/37* (2013.01); *A61K 8/39* (2013.01); *A61K 8/40* (2013.01); *A61K 8/8158* (2013.01); *A61K 8/86* (2013.01); *A61K 8/894* (2013.01); *A61Q 17/04* (2013.01); *A61K 2800/31* (2013.01); *A61K 2800/596* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 6,060,546 | A * | 5/2000 | Powell | A61K 8/042 424/64 |
| 2004/0175403 | A1* | 9/2004 | Lukenbach | A61K 8/39 424/401 |
| 2006/0128601 | A1* | 6/2006 | Pereira | A61K 8/4946 510/504 |
| 2008/0213322 | A1 | 9/2008 | Birman et al. | |

FOREIGN PATENT DOCUMENTS

| | | |
|---|---|---|
| FR | 2924930 A1 | 6/2009 |
| JP | 2006315986 A | 11/2006 |
| WO | 03/024412 A2 | 3/2003 |

OTHER PUBLICATIONS

European Search Report for EP 13190946.7, date May 12, 2014.
International Search Report and Written Opinion for PCT/EP2014/068169, date of mailing Dec. 19, 2014.
K. Kwetkat, Gemini Surfactant Blends for Personal Care Applications, SOFW-Journal, vol. 128, No. 4, Jan. 1, 2002, pp. 38, 40-42, 44, XP001536316.
Busch, P. et al., Das Phaenomen des Weisselns beim Auftragen Hautkosmetischer Formulierungen, (The phenomenon of "Whitening" when applying skin-cosmetic formulations) vol. 75, No. 75, Jan. 1, 1994, pp. 312-317, XP009177782 (Translation attached).
Database GNPD [Online], Mintel; Feb. 2014, Sport Kids Continuous Spray SPF50, XP002733446.

* cited by examiner

*Primary Examiner* — Robert A Wax
*Assistant Examiner* — Quanglong Truong
(74) *Attorney, Agent, or Firm* — Sandra B. Weiss

(57) ABSTRACT

A non-whitening sunscreen formulation for application to wet skin includes a surfactant system and organic UV absorbing materials where surfactant system includes a silicon based surfactant and a nonionic Gemini surfactant. Methods of making the sunscreen formulation are also included.

14 Claims, No Drawings

SUNSCREEN FORMULATIONS COMPRISING GEMINI SURFACTANTS AND SILICONE BASED SURFACTANTS

This application is a national stage filing under 35 U.S.C. §371 of PCT/EP2014/068169, filed Aug. 27, 2014, which claims priority to U.S. Provisional Patent Application No. 61/870,291 filed Aug. 27, 2013, and European Patent Application No. 13190946.7, filed Oct. 30, 2013, the contents of which are each incorporated herein by reference in their entireties.

FIELD OF THE INVENTION

The present invention relates to sunscreen compositions comprising a surfactant system and an organic UV absorbing material that can be applied to wet skin that has reduced or non-whitening on application and provides improved aesthetic properties. The surfactant system comprises a silicon based surfactant and a nonionic Gemini surfactant.

BACKGROUND OF THE INVENTION

Sunscreen compositions are typically categorized as either aqueous or non-aqeuous compositions. Aqueous sunscreen compositions are typically creams formed as emulsions containing the active UV absorbing compounds and additional ingredients such as waterproofing agents, fragrances, emollients and other skin care ingredients. Non-aqueous sunscreen compositions are those that are typically solvent-based compositions that can be formed as gels for topical application or sprayed-on, for example from an alcohol based solution of the ingredients.

In order to keep the emulsion stable in the cream, thickeners are generally utilized. The most common thickeners are formed from cross-linked acrylic acid and are commonly known as carbomers (e.g., Carbomer 940).

While emulsion based sunscreens contain water as the continuous phase, application of these sunscreens to wet skin does not generally pose much of an issue. However, with the advent of continuous spray sunscreens (i.e. ethanol based with very little to no water present), application to wet skin causes the organic UV absorbers to become insoluble in the water/ethanol mix. This phenomenon causes the applied sunscreen to become white (an un-desired aesthetic affect) and may even cause non-uniformity within the film upon drying.

Consequently, application of an emulsion to wet skin leaves the wearer's skin tacky and white until the sunscreen has completely dried. Accordingly, there is a need to provide a sunscreen that overcomes these undesirable effects.

SUMMARY OF THE INVENTION

In an aspect, the present invention relates to a sunscreen composition comprising a surfactant system and an organic UV absorbing material. The surfactant system comprises at least one silicon based surfactant and at least one nonionic Gemini surfactant.

In another aspect, the present invention relates to a method for reducing preparing a sunscreen composition comprising blending a surfactant system with an organic UV absorbing material. The surfactant system comprises at least one silicon based surfactant and at least one nonionic Gemini surfactant.

In yet another aspect, the present invention relates to a method of reducing the whitening effect of a spray-on sunscreen upon application to wet skin. The method comprises applying a sunscreen formulation to the skin wherein the sunscreen formulation comprises a surfactant system and an organic UV absorbing material and the surfactant system comprises at least one silicon based surfactant and at least one nonionic Gemini surfactant.

DETAILED DESCRIPTION OF THE INVENTION

The present invention generally relates to a sunscreen composition comprising a surfactant system and an organic UV absorbing material. The surfactant system comprises a silicon based surfactant and a nonionic Gemini surfactant. It has been found that the addition of the surfactant system to alcohol-based sunscreen formulations can surprisingly provide such sunscreen formulations, and, in particular, a spray-on sunscreen formulation, with reduced or non-whitening properties.

For purposes of this invention, solvent-based sunscreens are those that contain organic UV A and UV B absorbers which are completely soluble in the solvent system. By the term "completely soluble", it is meant that the organic UV absorbers and the solvent system form a homogeneous solution.

In an embodiment of the invention, the sunscreen compositions further comprise a solvent system. Suitable solvents include $C_1$-$C_4$ straight or branched chain alcohol, acetone, methyl acetate, butyl cellusolve, propylene glycol and mixtures thereof. In another embodiment, the solvent system is preferably an alcohol-based solvent system, such as methanol, ethanol, isopropanol either alone or in their combination.

Further, even small quantities of water can be present in the sunscreen formulation. In an embodiment, it is preferred that the solvent system be substantially anhydrous. For purposes of the present invention, "substantially anhydrous" means having less than about 5% water. In another embodiment of this invention, the spray-on sunscreen formulation may contain less than about 2% water, and in yet another embodiment preferably about 1% or less water.

The surfactant system of the sunscreen composition of the present invention includes at least two types of surfactants in order to exhibit the desired non-whitening property. The first type of surfactant is a silicon containing surfactant, such as PPG-12 Dimethicone (available from Momentive, Tarrytown, N.Y.) or Bis-Hydroxyethoxypropyl Dimethicone (available from Dow-Corning, Midland, Mich.) or mixtures thereof.

The second type of surfactant in the system is a nonionic Gemini surfactant, such as described in U.S. Pat. No. 6,204,297 B1, which is incorporated by reference in its entirety herein. In an embodiment, suitable nonionic Gemini surfactants which are useful in the present invention include, but are not limited to, those of the formula:

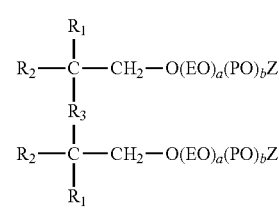

I wherein $R_1$ is independently H or a $C_1$ to $C_{22}$ alkyl, $R_2$ is H or $C_1$ to $C_{22}$ alkyl and $R_3$ is —C(O)—, S, $SO_2$, S—S or $D_1$-$R_4$-$D_1$ or $R_4$-$D_1$-$R_4$ wherein $R_4$ is independently a $C_1$-$C_{10}$ alkyl group, —C(O)—, —$R_5[O(EO)_a(PO)_b]$—, —O—$R_5$—O—, or aryl, e.g. phenyl, and $D_1$ is independently —O—, —S—, —S—S—, —$SO_2$—, —C(O)—, a polyether group [—$O(EO)_a(PO)_b$—], an amide group [—C(O)N($R_6$)—], an amino group [—N($R_6$)—], —O—$R_5$—O—, or aryl, $(EO)_a(PO)_b$ is a polyether group and Z is a $C_1$-$C_4$ alkyl, or an alkylaryl or hydrogen. When $D_1$ is an amino group, then $R_6$, $R_4$, and $D_1$ can be part of a heterocyclic ring. $R_5$ and $R_6$ are a $C_1$ to $C_{10}$ alkyl, aryl, or alkylaryl.

As described herein, EO represents ethyleneoxy radicals and PO represents propyleneoxy radicals, a and b are numbers of from 0 to 100. In an embodiment, a is preferably from about 0 to about 30 and b is preferably from about 0 to 10, wherein the sum of a and b is at least 1, and the EO and PO radicals can be randomly mixed or can be discrete blocks.

With respect to the formulae described herein, the term "alkyl" includes substituted alkyl, especially the hydroxy substituted derivatives thereof as well as straight and branched chains. When Z is hydrogen, the Gemini surfactants are nonionic and when Z is a $C_1$ to $C_4$ alkyl, or an alkylaryl, they become low foaming nonionics.

The compounds of Formula I are more fully described in U.S. Pat. No. 5,643,864, which is incorporated by reference in its entirety herein.

In an embodiment of the present invention, particularly useful Gemini surfactants include, but are not limited to, nonionic surfactants of the following formulae:

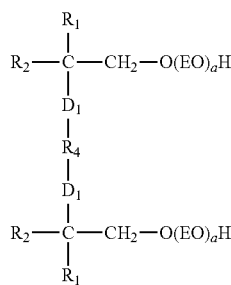

II wherein $R_1$ represents H or is a $C_1$ to $C_{22}$ alkyl or aryl, $R_2$ is a $C_1$ to $C_{22}$ alkyl or aryl, a and $R_4$ are as described above and $D_1$ is O, S, or N—$R_6$ wherein $R_6$ is $C_1$-$C_{10}$ alkyl, aryl or alkylaryl.

In another embodiment, the nonionic Gemini surfactants suitable for use in the present invention are more preferably selected from the following structures:

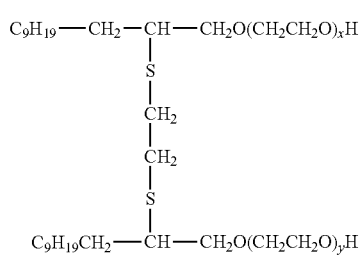

III

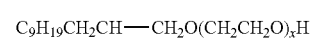

IV

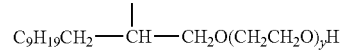

V where x+y=z, and z is equal to a number from 1 to 22.

In a particularly preferred embodiment, the nonionic Gemini surfactant is selected from Di-PPG2-Myreth-10 Adipate, Di-Glycerol 2,9-Dihexyldecanedioate or mixtures thereof.

In an embodiment, preferably the weight ratio of silicon surfactant to Gemini surfactant is from about 40:60 to about 60:40, and in another embodiment, more preferably the ratio is from about 55:45 to about 45:55 (respectively) to obtain the non-whitening properties.

In an embodiment of the invention, preferably the amount of surfactant system in the total formulation (percent by weight including the solvent) is greater than about 10%. In another embodiment, the surfactant system will more preferably be greater than about 15%, and in yet another embodiment, even more preferably be greater than about 20% by weight in the total formulation (including the solvent).

For purposes of this invention, in order to determine whether a sunscreen formulation is "non-whitening", the formulations were subjected to two test methods. The first method is a subjective test in which a person's forearm is wetted with water just prior to the application of the spray-on sunscreen. If the user detects any whiteness on application, then the formulation did not pass. The second method is to measure the transmission of light (turbidity) through a film of the formulation after being contacted with water (for details on the method see Example 2 below). The average light transmission of the film should be greater than about 5% transmission when measured by the Turbiscan as described in Example 2, at 25° C. when in contact with a film of water. In an embodiment of this invention, the average light transmission is greater than about 7.5%, and in another embodiment more preferably greater than about 10% when measured by the Turbiscan at 25° C. when in contact with a film of water.

In addition to the surfactant system, the sunscreen formulations of the present invention also include organic UV absorbers. For purposes of the present invention, a "UV absorber" shall include all of those organic materials, singly or in combination, that are regarded as acceptable for absorbing UV radiation. Such compounds are generally described as being UV-A, UV-B, or UV-A/UV-B active agents. Approval by a regulatory agency is generally required for inclusion of active agents in formulations intended for human use. Those active agents which have been or are currently approved for sunscreen use in the United States include organic substances including, without limitation, para aminobenzoic acid, avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, diethanolamine methoxycinnamate, digalloy trioleate, ethyl dihydroxypropyl PABA, glyceryl aminobenzoate, lawsone with dihydroxyacetone, red petrolatum. Examples of additional sunscreen actives that have not yet been approved in the US but are allowed in formulations sold outside of the US include ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate and mixtures thereof. However, as the list of approved sunscreens is currently expanding, those of ordinary skill will recognize that the invention is not limited to sunscreen active agents currently approved for human use but it is readily applicable to those that may be allowed in the future.

In addition to the UV absorbers and the above-described surfactants, film forming polymers, which can be either synthetic or natural polymers can be added to the formulation. Suitable non-limiting examples of these additional film forming polymers include but are not limited to: from Akzo Nobel Surface Chemistry LLC, Bridgewater N.J., AMPHOMER and AMPHOMER LV-71 polymers (octylacrylamide/acrylates/butylaminoethyl methacrylate copolymer), AMPHOMER HC polymer (acrylates/octylacrylamide copolymer) BALANCE 0/55, BALANCE CR and DERMACRYL AQF polymers (acrylates copolymer), BALANCE 47 polymer (octylacrylamide/butylaminoethyl methacrylate copolymer), RESYN 28-2930 polymer (VA/crotonates/vinyl neodecanoate copolymer), RESYN 28-1310 polymer (VA/Crotonates copolymer), FLEXAN polymers (sodium polystyrene sulfonate), DynamX polymer (polyurethane-14 (and) AMP-Acrylates copolymer), RESYN XP polymer (acrylates/octylacrylamide copolymer), STRUCTURE 2001 (acrylates/steareth-20 itaconate copolymer) and STRUCTURE 3001 (acrylates/ceteth-20 itaconate copolymer); from ISP, OMNIREZ-2000 (PVM/MA half ethyl ester copolymer), GANEX P-904 (butylated PVP), GANEX V-216 (PVP/hexadecene copolymer) GANEX V-220 (PVP/eicosene copolymer), GANEX WP-660 (tricontanyl PVP), GANTREZ A425 (butyl ester of PVM/MA copolymer), GANTREZ AN-119 PVM/MA copolymer, GANTREZ ES 225 (ethyl ester of PVM/MA copolymer), GANTREZ ES425 (butyl ester of PVM/MA copolymer), GAFFIX VC-713 (vinyl caprolactam/PVP/dimethylaminoethyl methacrylate copolymer), GAFQUAT 755 (polyquaternium-11), GAFQUAT HS-100 (polyquaternium-28) AQUAFLEX XL-30 (Polyimide-1), AQUAFLEX SF-40 (PVP/Vinylcaprolactam/DMAPA Acrylates Copolymer), AQUAFLEX FX-64 (Isobutylene/Ethylmaleimide/Hydroxyethylmaleimide Copolymer), ALLIANZ LT-120 (Acrylates/C1-2 Succinates/Hydroxyacrylates Copolymer), STYLEZE CC-10 (PVP/DMAPA Acrylates Copolymer), STYLEZE 2000 (VP/Acrylates/Lauryl Methacrylate Copolymer), STYLEZE W-20 (Polyquaternium-55), Copolymer Series (PVP/Dimethylaminoethylmethacrylate Copolymer), ADVANTAGE S and ADVANTAGE LCA (VinylcaprolactamNP/Dimethylaminoethyl Methacrylate Copolymer), ADVANTAGE PLUS (VA/Butyl Maleate/Isobornyl Acrylate Copolymer); from BASF, ULTRAHOLD STRONG (acrylic acid/ethyl acrylate/t-butyl acrylamide), LUVIMER 100P (t-butyl acrylate/ethyl acrylate/methacrylic acid), LUVIMER 36D (ethyl acrylate/t-butyl acrylate/methacrylic acid), LUVIQUAT HM-552 (polyquaternium-16), LUVIQUAT HOLD (polyquaternium-16), LUVISKOL K30 (PVP) LUVISKOL K90 (PVP), LUVISKOL VA 64 (PVPNA copolymer) LUVISKOL VA73W (PVPNA copolymer), LUVISKOL VA, LUVISET PUR (Polyurethane-1), LUVISET Clear (VP/MethacrylamideNinyl Imidazole Copolymer), LUVIFLEX SOFT (Acrylates Copolymer), ULTRAHOLD 8 (Acrylates/Acrylamide Copolymer), LUVISKOL Plus (Polyvinylcaprolactam), LUVIFLEX Silk (PEG/PPG-25/25 Dimethicone/Acrylates Copolymer); from Amerchol, AMERHOLD DR-25 (acrylic acid/methacrylic acid/acrylates/methacrylates); from Rohm&Haas, ACUDYNE 258 (acrylic acid/methacrylic acid/acrylates/methacrylates/hydroxyl ester acrylates; from Mitsubishi and distributed by Clariant, DIAFORMER Z-301, DIAFORMER Z-SM, and DIAFORMER Z-400 (methacryloyl ethyl betaine/acrylates copolymer), ACUDYNE 180 (Acrylates/Hydroxyesters Acrylates Copolymer), ACUDYNE SCP (Ethylenecarboxyamide/AMPSA/Methacrylates Copolymer), and the ACCULYN rheological modifiers; from ONDEO Nalco, FIXOMER A-30 and FIXOMER N-28 (INCI names: methacrylic acid/sodium acrylamidomethyl propane sulfonate copolymer); from Noveon, FIXATE G-100 (AMP-Acrylates/Allyl Methacrylate Copolymer), FIXATE PLUS (Polyacrylates-X), CARBOPOL Ultrez 10 (Carbomer), CARBOPOL Ultrez 20 (Acrylates/C10-30 Alkyl Acrylates Copolymer), AVALURE AC series (Acrylates Copolymer), AVALURE UR series (Polyurethane-2, Polyurethane-4, PPG-17/IPDI/DMPA Copolymer); polyethylene glycol; water-soluble acrylics; water-soluble polyesters; polyacrylamides; polyamines; polyquaternary amines; styrene maleic anhydride (SMA) resin; polyethylene amine; and other conventional polymer that is polar solvent soluble or that can be made soluble through neutralization with the appropriate base.

The sunscreen formulations of the present invention may contain a wide range of additional, optional components, which are referred to herein as "cosmetic components", but which can also include components generally known as pharmaceutically active agents. The CTFA Cosmetic Ingredient Handbook, Seventh Edition, 1997 and the Eighth Edition, 2000, which is incorporated by reference herein in its entirety, describes a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, reducing agents, skin bleaching agents, skin-conditioning agents (emollient, humectants, miscellaneous, and occlusive), skin protectants, solvents, foam boosters, hydrotropes, solubilizing agents, suspending agents (non-surfactant), sunscreen agents, ultraviolet light absorbers, SPF boosters, waterproofing agents, and viscosity increasing agents (aqueous and non-aqueous).

In an embodiment, the sunscreen formulation may optionally also include one or more inorganic and/or particulate additive UV blocker materials to block the UV light from reaching the skin. The most popular of these are $TiO_2$ and $ZnO$ and $SiO_2$. Other particulates have also been described in the literature, such as starch and cellulose as all natural UV protective additives. It is recognized, however, that addition of these types of materials to the sunscreen formulations of the present invention, could pose problems with clogging of spray nozzles for spray-on sunscreen formulations. Nevertheless, where these difficulties are overcome, such particles would not interfere with the non-whitening properties of the formulations described herein.

Spray applications of the present invention require a mechanical device or pressurized aerosol container to generate the spray. The devices can be manual such as a pump or squeeze bottle or typical aerosol device such as bag-on-nozzle or pressurized can. If a pressurized can is used then the sunscreen formulations of the present invention may further include a propellant. Such propellants include, without limitation, ethers, such as dimethyl ether; one or more lower boiling hydrocarbons such as $C_3$-$C_6$ straight and branched chain hydrocarbons, for example, propane, butane, and isobutane; halogenated hydrocarbons, such as, hydrofluorocarbons, for example, 1,1-difluoroethane and 1,1,1,2-tetrafluoroethane, present as a liquefied gas; and the compressed gases, for example, nitrogen, air and carbon dioxide. In an embodiment of the invention, the propellant is present in an amount of about 25% to about 60% by weight of the hair fixative composition including the solvent system. In a further embodiment, the propellant is present in an amount of about 30% to about 50% by weight. The propellant is not considered in the formulation weight when considering ratios and percentages. Alternatively, in certain spray applications, such as bag-on-nozzle spray applications or pump spray applications, such optional propellants are not required.

Unless otherwise specified, all the percentages listed above are based on the total weight of the formulation. One of skill in the art would recognize that some ingredients are not provided as dry materials, so the percentages of those ingredient are meant as the dry solids as a percent of the total formulation. Alternatively stated, the water or solvent in an ingredient is not taken into account for purposes of calculating the percentage in the formulation.

In a further aspect, the present invention further provides a method for preparing a sunscreen composition. The method provides blending an effective amount of a surfactant system with an effective amount of an organic UV absorbing material. The surfactant system comprises at least one silicon based surfactant and at least one nonionic Gemini surfactant.

In addition, the present invention also provides a method of reducing the whitening effect so as to achieve a non-whitening effect of a spray-on sunscreen formulation when applied to wet skin. The method provides applying the sunscreen formulation to the wet skin. The sunscreen formulation comprises a surfactant system and an organic UV absorbing material. The surfactant system comprises at least one silicon based surfactant and at least one nonionic Gemini surfactant.

The following examples are intended to exemplify the present invention but are not intended to limit the scope of the invention in any way. The breadth and scope of the invention are to be limited solely by the claims appended hereto.

EXAMPLES

Ingredients

TABLE 1

| TRADE NAME | INCI NAME | MANUFACTURER |
|---|---|---|
| Dermacryl 79 | Acrylates/Octylacrylamide Copolymer | Akzo Nobel Surface Chemistry LLC, Bridgewater NJ |
| Neo Heliopan ® 357 | Avobenzone | Symrise Inc. 300 North Street Teterboro, NJ 07608 |
| Neo Heliopan ® HMS | Homosalate | Symrise Inc. 300 North Street Teterboro, NJ 07608 |
| Neo Heliopan ® OS | Ethylhexyl Salicylate | Symrise Inc. 300 North Street Teterboro, NJ 07608 |
| Neo Heliopan ® 303 | Octocrylene | Symrise Inc. 300 North Street Teterboro, NJ 07608 |
| Neo Heliopan ® BB | Benzophenone-3 | Symrise Inc. 300 North Street Teterboro, NJ 07608 |
| DC 5562 Carbinol Fluid | Bis-Hydroxyethoxypropyl Dimethicone | Dow Corning, PO Box 994 MIDLAND MI 48686-0994 |
| Cromollient SCE-LQ-(MH) | Di-PPG2-Myreth-10 Adipate | Croda Inc, 300-A Columbus Circle Edison, NJ 08837 |
| Wickenol 707 | PPG-30 Cetyl Ether | Alzo, International, 650 Jernee Mill Road Sayreville, NJ 08872 |
| Permethyl 101A | Isohexadecane | Presperse Corp., 635 pierce street • somerset, NJ 08873 |
| Trivent OC-143 | Myreth-3 Octanoate | Alzo International, 650 Jernee Mill Road Sayreville, NJ 08872 |
| Silsoft 900 | PPG-12 Dimethicone | Momentive |
| Dow Corning 225 Fluid | Dimethicone | Dow Corning, PO Box 994 MIDLAND MI 48686-0994 |
| Dow Corning 200 Fluid | Dimethicone | Dow Corning, PO Box 994 MIDLAND MI 48686-0994 |
| Permethyl 99A | Isododecane | Presperse Corp., 635 pierce street • somerset, NJ 08873 |
| Arlamol PS15E | PPG-15 Stearyl Ether | Croda Inc, 300-A Columbus Circle Edison, NJ 08837 |

TABLE 1-continued

| TRADE NAME | INCI NAME | MANUFACTURER |
|---|---|---|
| Hetester PHA | Propylene Glycol Isoceteth-3 Acetate | Alzo International, 650 Jernee Mill Road Sayreville, NJ 08872 |
| Permethyl 102A | Isoeicosane | Presperse Corp., 635 pierce street • somerset, NJ 08873 |

Example 1

Preparation of an Ethanol Based Sunscreen

Part A—A solution of the film forming polymer and UV absorbing actives was prepared by mixing the following ingredients in a glass beaker until uniform.

TABLE 2

| SD Alcohol 40B (ethanol) | 52.00% |
|---|---|
| Acrylates/Octylacrylamide Copolymer | 2.00% |
| Avobenzone | 3.00% |
| Homosalate | 12.00% |
| Ethylhexyl Salicylate | 5.00% |
| Octocrylene | 2.00% |
| Benzophenone-3 | 4.00% |

Part B—In the following examples (identified as comparative examples), where the surfactant system was a single compound it was added to part A above with good mixing to make a uniform sample. In the remaining examples (both comparative and those in accordance with the present invention), where the surfactant system was a blend of two or more individual surfactants, the surfactant system was prepared by blending the surfactants prior to addition to part A. In examples where less than 20% of the surfactant system was tested, the additional weight was compensated for by addition of the appropriate amount of ethanol.

The samples shown in Table 3 (below) were added to part A and mixed to obtain a uniform solution of 100 mLs total and then placed is a pump spray bottle which delivers 200 microliter with each pump. The skin on test subjects arms were then sprayed (using a pump spray bottle) with water to thoroughly wet the skin. The test sample was then sprayed onto the wet skin (without allowing the skin any time to dry) and the resulting film on sunscreen on the skin was observed. Subjective evaluation of various surfactant systems are shown below in Table 3.

TABLE 3

Comparison of surfactant systems for whitening on wet skin

| Example # | Surfactant(s) | Addition level | Whitened on wet skin spray application |
|---|---|---|---|
| C1 | PPG30 Cetyl ether | 20% | Yes—slightly |
| C2 | PPG30 Cetyl ether | 10% | Yes |
| C3 | Isohexadecane | 20% | Yes |
| C4 | Myreth-3-octanoate | 20% | Yes—slightly |
| C5 | PPG30 Cetyl dimethicone + PPG12 Dimethicone | 5% + 5% | Yes |
| C6 | PPG30 Cetyl ether + DC225 | 5% + 5% | Yes |
| C7 | PPG30 Cetyl ether + DC200 | 5% + 5% | Yes |
| C8 | PPG30 Cetyl ether + Isododecane | 5% + 5% | Yes |
| C9 | PPG12 Dimethicone + Isododecane | 5% + 5% | Yes |
| C10 | PPG15 Stearyl ether | 10% | Yes |
| C11 | PPG15 Stearyl ether | 15% | Yes |
| C12 | PPG15 Stearyl ether | 20% | Yes—slightly |
| C13 | Propylene glycol isoceteth-3 acetate | 20% | Yes—slightly |
| C14 | Propylene glycol isoceteth-3 acetate | 10% | Yes |
| C15 | DC5562 + Isoeicosane + PPG-30 cetyl ether | 2.5% + 2.5% + 5% | Yes |
| C16 | Isoeicosane + PPG-12 Dimethicone | 5% + 5% | Yes |
| C17 | PPG30 cetyl ether + PPG15 stearyl ether | 9% + 1% | Yes |
| C18 | PPG30 cetyl ether + PPG15 stearyl ether | 8% + 2% | Yes |
| C19 | PPG30 cetyl ether + PPG12 dimethicone | 9% + 1% | Yes |
| C20 | PPG30 cetyl ether + PPG12 dimethicone | 8% + 2% | Yes |
| 21 | Bis-Hydroxyethoxypropyl Dimethicone + Di-PPG2-Myreth-10 Adipate | 10% + 10% | No |
| C22 | Bis-Hydroxyethoxypropyl Dimethicone | 20% | Yes—slightly |
| C23 | Di-PPG2-Myreth-10 Adipate | 20% | Yes—slightly |
| C24 | Bis-Hydroxyethoxypropyl Dimethicone + Di-PPG2-Myreth-10 Adipate | 15% + 5% | Yes—slightly |
| C25 | Bis-Hydroxyethoxypropyl Dimethicone + Di-PPG2-Myreth-10 Adipate | 5% + 15% | Yes—slightly |
| 26 | Bis-Hydroxyethoxypropyl Dimethicone + Di-PPG2-Myreth-10 Adipate | 12% + 8% | No |

TABLE 3-continued

Comparison of surfactant systems for whitening on wet skin

| Example # | Surfactant(s) | Addition level | Whitened on wet skin spray application |
|---|---|---|---|
| 27 | Bis-Hydroxyethoxypropyl Dimethicone + Di-PPG2-Myreth-10 Adipate | 8% + 12% | No |

*Samples identified with the letter C are comparative examples.

The results of the subjective testing revealed that Examples 21, 26 and 27, which included both a silicon-based surfactant and a Gemini surfactant in the ratio of about 60:40 to about 40:60 provide the non-whitening effect in these organic sunscreen formulations. Further, the minimum level of this specific surfactant system that exhibited the non-whitening effect was greater than 10% in the sunscreen formulation.

Example 2

Transmittance of Water/Sunscreen Films

Turbiscan % Transmission—Ethanol Based Sunscreen Test Method
  Equipment: Turbiscan™ LAB
  by Formulaction SA, 10, impasse Borde Basse, 31240 L'Union—France.
  Turbiscan Vial 2 in. long, ~1 in. diameter
  Measurement temperature=25 C.
  Measurement of the transmission of the water/sunscreen film was conducted using the Turbiscan instrument with the following procedure to simulate what happens on the surface of the skin. A total of 3 mL of ethanol-based sunscreen was dispersed with a pipette in a circular application motion on the inside edge of a Turbiscan vial measuring 2 inches long and a diameter ~1 inch. The vial was slowly rotated horizontally after the 3 mL of ethanol-based sunscreen is dispensed in order to coat the entire height of inner surface of the vial for 15 seconds to insure that the film is uniformly distributed on the inside of the vial. Any excess sunscreen was allowed to drain from the vial by inverting the vial and placing the vial upside down on a paper towel for 5 minutes. This also allowed the majority of ethanol to evaporate. Using a 200 microliter pump spray bottle, 3 pumps of DI water were applied into the ethanol sunscreen-coated vial, and the Turbiscan program was immediately run to measure the percentage of light transmission of the vial along the entire length of the vial.

The results shown in Table 4 are from two commercially available sunscreen products currently on the market (Neutrogena wetskin sunblock spray SPF50 and Coppertone sunscreen continuous spray wet'n'clear SPF30) and a control which was just water with no sunscreen added. Measurements are taken by the Turbiscan instrument at 0.1 mm interval and are reported below as the average transmission along the entire vial.

TABLE 4

Transmittance of water/sunscreen films

| Sample | Average Transmission |
|---|---|
| Blank | 28.38 |
| Example 21 | 12.28 |
| Neutrogena | 3.93 |
| CopperTone | 2.78 |

The results from Table 4 show that the combination of the surfactant blend in the sunscreen formulation, i.e. Example 21, provides superior film forming capabilities with no whitening when applied to wet skin as compared to the leading commercial brands tested.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described herein, the invention is not intended to be limited to the details shown. Rather, various modifications may be made in the details within the range and scope of equivalents of the claims and without departing from the spirit and scope of the invention.

We claim:

1. A sunscreen composition comprising:
  a surfactant system;
  a solvent system; and
  an organic UV absorbing material,
wherein the surfactant system comprises at least one silicon based surfactant and at least one nonionic Gemini surfactant, wherein said sunscreen composition is substantially anhydrous, and wherein said organic UV-absorbing material is soluble in said solvent system.

2. The sunscreen composition of claim 1 where the weight ratio of the silicon based surfactant to the nonionic Gemini surfactant is from 60:40 to 40:60.

3. The sunscreen composition of claim 2 wherein the surfactant system is present in the composition an amount of 10 wt % or greater based on the weight of the sunscreen composition.

4. The sunscreen composition of claim 1 wherein the silicon based surfactant is PPG-12 Dimethicone or Bis-Hydroxyethoxypropyl Dimethicone or mixtures thereof.

5. The sunscreen composition of claim 1 wherein the nonionic Gemini surfactant has the following formula (I):

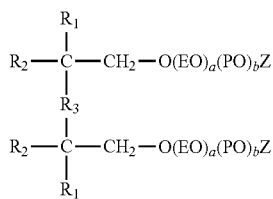

(I)

wherein $R_1$ is independently H or a $C_1$ to $C_{22}$ alkyl, $R_2$ is H or $C_1$ to $C_{22}$ alkyl and $R_3$ is —C(O)—, S, $SO_2$, S—S or $D_1$-$R_4$-$D_1$ or $R_4$-$D_1$-$R_4$ wherein $R_4$ is independently a $C_1$-$C_{10}$ alkyl group, —C(O)—, —$R_5$[O(EO)$_a$(PO)$_b$]—, —O—$R_5$—O— or aryl, and $D_1$ is independently —O—, —S—, —S—S—, —$SO_2$—, —C(O)—, a polyether group [O(EO)$_a$(PO)$_b$—], an amide group [—C(O)N($R_6$)—], an amino group [—N($R_6$)—], —O—$R_5$—O—, or aryl, (EO)$_a$(PO)$_b$ is a polyether group and Z is a $C_1$-$C_4$ alkyl, or an alkylaryl or hydrogen.

6. The sunscreen composition of claim 5 wherein the nonionic Gemini surfactant is Di-PPG2-Myreth-10 Adipate or Di-Glycerol 2,9-Dihexyldecanedioate or mixtures thereof.

7. The sunscreen composition of claim 1 wherein said solvent system is an alcohol solvent system having about 5% water or less.

8. The sunscreen composition of claim 7 wherein the alcohol solvent system is one or more $C_1$-$C_4$ straight or branched chain alcohols.

9. The sunscreen composition of claim 7 wherein the alcohol solvent system is selected from the group consisting of methanol, ethanol, isopropanol and mixtures thereof.

10. The sunscreen composition of claim 1 further comprising a film forming polymer.

11. The sunscreen composition of claim 1 wherein the composition is a spray-on sunscreen.

12. The sunscreen composition of claim 1 wherein the organic UV absorbing material is selected from the group consisting of para aminobenzoic acid, avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, diethanolamine methoxycinnamate, digalloy trioleate, ethyl dihydroxypropyl PABA, glyceryl aminobenzoate, lawsone with dihydroxyacetone, red petrolatum, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylheximino triazine, drometrizole trisiloxane, methylene bis-benzotriazolyl tetramethylbutylphenol, and bis-ethylhexyloxyphenol methoxyphenyltriazine, 4-methylbenzylidenecamphor, isopentyl 4-methoxycinnamate and mixtures thereof.

13. The sunscreen composition of claim 1 wherein the composition further comprises one or more inorganic and/or particulate additive UV blocker materials.

14. A method for preparing a sunscreen composition according to claim 1 comprising blending an effective amount of the surfactant system with an effective amount of the organic UV absorbing material.

\* \* \* \* \*